United States Patent
Fitzgerald et al.

(10) Patent No.: US 9,101,341 B2
(45) Date of Patent: Aug. 11, 2015

(54) CRANIAL BASE IMPLANT DEVICE

(71) Applicants: Patrick J. Fitzgerald, Poway, CA (US); R. Todd McKinney, Rancho Santa Fe, CA (US); Jasper Benke, San Diego, CA (US); Sean Jeffrey Mitchell, Carlsbad, CA (US)

(72) Inventors: Patrick J. Fitzgerald, Poway, CA (US); R. Todd McKinney, Rancho Santa Fe, CA (US); Jasper Benke, San Diego, CA (US); Sean Jeffrey Mitchell, Carlsbad, CA (US)

(73) Assignee: Patrick J. Fitzgerald, Poway, CA (US)

( * ) Notice: Subject to any disclaimer, the term of this patent is extended or adjusted under 35 U.S.C. 154(b) by 0 days.

(21) Appl. No.: 14/108,845

(22) Filed: Dec. 17, 2013

(65) Prior Publication Data

US 2014/0172014 A1    Jun. 19, 2014

Related U.S. Application Data (63) Continuation of application No. PCT/US2013/075424, filed on Dec. 16, 2013.

(60) Provisional application No. 61/738,305, filed on Dec. 17, 2012.

(51) Int. Cl.
  *A61F 2/02* (2006.01)
  *A61B 17/00* (2006.01)
  *A61F 2/28* (2006.01)
  *A61B 19/00* (2006.01)

(52) U.S. Cl.
  CPC ........... *A61B 17/0057* (2013.01); *A61F 2/2875* (2013.01); *A61B 2017/00659* (2013.01); *A61B 2019/208* (2013.01); *A61F 2002/2885* (2013.01)

(58) Field of Classification Search
  CPC ........... A61F 2/2875; A61F 2002/2878; A61F 2002/2882; A61F 2002/2885; A61F 2002/2889; A61B 2019/208
  USPC ........................................................ 623/17.19
  See application file for complete search history.

(56) References Cited

U.S. PATENT DOCUMENTS

| | | | | |
|---|---|---|---|---|
| 4,245,359 | A * | 1/1981 | Stuhmer | 606/95 |
| 6,491,725 | B1 * | 12/2002 | Koyama et al. | 623/17.19 |
| 7,833,253 | B2 * | 11/2010 | Ralph et al. | 606/283 |
| 8,287,567 | B2 | 10/2012 | Gazzani et al. | |
| 8,882,832 | B2 * | 11/2014 | Padsalgikar et al. | 623/8 |
| 2006/0224242 | A1 | 10/2006 | Swords | |
| 2007/0270841 | A1 | 11/2007 | Badie | |
| 2010/0036413 | A1 | 2/2010 | Nakaji | |
| 2011/0087232 | A1 | 4/2011 | Levatich | |
| 2011/0118839 | A1 * | 5/2011 | Nutter | 623/16.11 |

OTHER PUBLICATIONS

International Search Report and Written Opinion for related international application No. PCT/US2013/075424, mailed Apr. 3, 2014, in 18 pages.

\* cited by examiner

*Primary Examiner* — Bruce E Snow
*Assistant Examiner* — Brian Dukert
(74) *Attorney, Agent, or Firm* — Procopio, Cory, Hargreaves & Savitch LLP (57) ABSTRACT

A device for closing a hole in a sphenoid bone that acts as a barrier between a sella turcica and a sphenoid sinus is disclosed. The device includes a cap and a stem. The cap is formed of a deformable material. The cap includes a contact surface and an upper surface. The contact surface forms a base of the cap and includes an outer perimeter. The upper surface includes an apex offset from the contact surface. The upper surface extends from the apex to the outer perimeter. The stem extends from the contact surface in a direction opposite the apex.

30 Claims, 6 Drawing Sheets

CRANIAL BASE IMPLANT DEVICE

RELATED APPLICATION

The present application claims the benefit of co-pending U.S. provisional patent application no. 61/738,305 filed on Dec. 17, 2012, the contents of which are incorporated herein by reference in their entirety.

TECHNICAL FIELD

The present invention relates generally to an implant device used to close a hole or defect in the sphenoid bone that acts as a barrier between the sella turcica and the sphenoid sinus.

BACKGROUND

Endoscopic transphenoidal pituitary tumor removal involves removing the floor of the sella turcica, opening the dura mater, and then removing the tumor with a variety of microsurgical techniques. These tumors can extend beyond the sella turcica and intwine with the meninges. Surgical removal of a tumor may disrupt the meninges, leading to the leakage of spinal fluid into the surgical field. Because the spinal fluid is under pressure, the fluid may continue to leak and maintain a communication between the intracranial space and the nasal/sinus space which may lead to conditions such as pneumocephalus, encephalitis, and meningitis.

During transphenoidal surgeries such as endoscopic transphenoidal pituitary tumor removal, a surgeon typically re-creates the barrier between the sphenoid sinus and sella turcica to prevent the spinal fluid leak and communication between the intracranial space and the nasal/sinus space. The surgeon generally uses an inlay, an overlay, or a combination of the two to re-create the barrier.

Inlay materials are placed on the brain side of the sella turcica. Inlay materials serve as structural support to counter the ongoing downward forces of the spinal fluid and meninges resulting from spinal fluid pressure and gravity. Inlay materials include bone, cartilage, and other less structurally sound materials such as fascia, pericardium, or dura harvested from the patient, or provided from a tissue bank. Bone and cartilage may provide significant support to prevent the slow, persistent herniation of meninges in the days and weeks after surgery leading to cerebrospinal fluid leaks. However, bone is difficult to work with due to sharp edges that may need to be removed, and due to the small custom shape needed to be created. The bone needs to be sized larger than the hole, making it difficult to place through the craniotomy. Patient cartilage is often too weak, and cracks when handling. While cadaveric rib cartilage is nearly ideal, it is a bit too rigid and time consuming to customize. Cadaveric rib cartilage is also not readily available, and is expensive.

Overlay materials do not provide long lasting structural support. Some overlays "plug" the hole using fat grafts, cellulose packing materials, or injectable glues. Other overlays cover the hole with fascia, dura, or mucosal grafts. Overlay materials such as mucosa, fat, gel foam, surgical glue, collagen, etc are easy to place and readily available. Fat requires a separate abdominal incision. These materials provide no structural support and rely on the hope that tissue ingrowth and healing will occur before the herniation of meninges and cerebrospinal fluid overcome them. Overlays are often sufficient for small meningeal penetrations; however, for medium to larger cerebrospinal fluid leaks, overlays are generally insufficient.

Overlays often lead to delayed cerebrospinal fluid leaks. The tissue used in the overlays often resorbs or mobilizes out of position with development of a cerebrospinal fluid leak.

U.S. patent application No. 2007/0270841 to B. Badle discloses implantable devices that may be positioned, for example, into the sphenoid sinus or sella turcica of a subject. In certain embodiments, the implantable devices comprise a center plate and a plurality of protruding arms extending from the center plate, both of which may be composed of bioresorbable material. In particular embodiments, the implantable devices are configured to help reconstruct the sellar floor after it has been damaged in order to prevent cerebrospinal fluid leaks.

SUMMARY

A device and method for closing a hole in a sphenoid bone that acts as a barrier between a sella turcica and a sphenoid sinus is disclosed. In one embodiment, the device includes a cap and a stem. The cap is formed of a deformable material. The cap includes a contact surface and an upper surface. The contact surface forms a base of the cap and includes an outer perimeter. The upper surface includes an apex offset from the contact surface. The upper surface extends from the apex to the outer perimeter. The stem extends from the contact surface in a direction opposite the apex.

A further embodiment includes a method for locating a device in an inlay position in the sella turcica. The device includes a cap formed of deformable material and a stem extending from the cap. The method includes gripping the device using a surgical tool. The method also includes introducing the device into the sphenoid sinus. The method further includes passing the device through a hole in the sphenoid bone by deforming the cap. The method still further includes locating the device with its original shape such that the cap is inside the sella turcica and a contact surface of the cap is in contact with the sphenoid bone about the hole.

DETAILED DESCRIPTION

The device disclosed herein includes a mushroom or conical shaped compressible or deformable biocompatible material soft enough to be atraumatic to bone and surrounding neurovascular structures, yet rigid enough to hold form and provide support after insertion into the sella turcica through a hole smaller than an outer diameter of the contact surface or the maximum width of the device.

Figure 1:
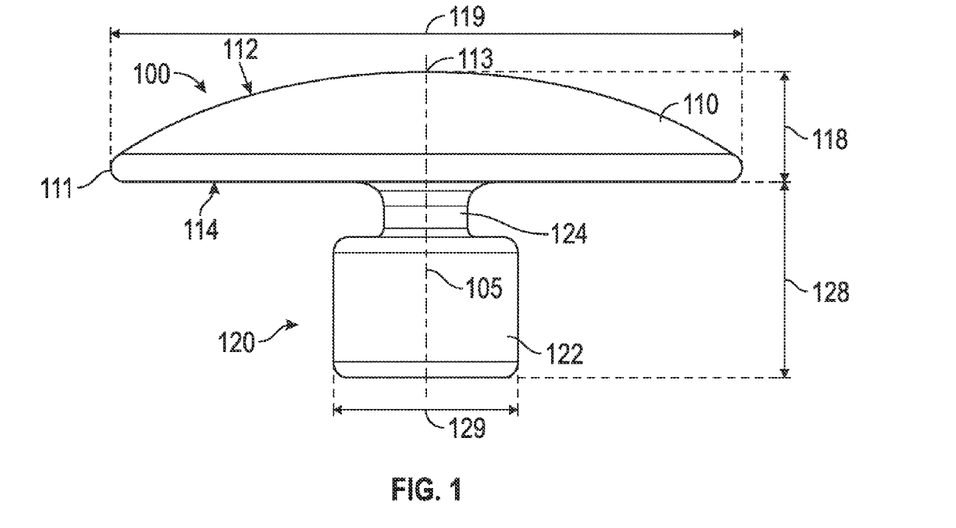
FIG. 1 is a side view of an exemplary embodiment of a cranial base implant device.

FIG. 1 is a side view of an exemplary embodiment of a cranial base implant device ("device") 100. Device 100 includes a cap 110 and a stem 120. Cap 110 may be rounded and may have a spherical, ellipsoidal or conical shape. The ellipsoidal shapes may include oblate and prolate spheroids. In the embodiment shown in FIG. 1, cap 110 is the shape of a spherical cap, a region of a sphere above a given plane; more particularly cap 110 is a spherical cap with a cap height 118 less than the radius of the sphere. In some embodiments, cap 110 is the shape of a hemisphere, a spherical cap with the plane cutting through the center of the sphere. In other embodiments, cap 110 is a spherical cap with a cap height 118 substantially smaller than the radius of the sphere resulting in a plate like cap 110 with a slightly domed upper surface 112. The cap 110 includes a cap width 119, which is the largest width of cap 110, which may be at the base of the spherical cap and may be the diameter of the base of the spherical cap. In one embodiment, cap width 119 is from 6 millimeters to 20 millimeters. In another embodiment, cap width 119 is from 20 millimeters and 40 millimeters. In yet another embodiment, cap width 119 is from 6 millimeters to 40 millimeters. In still another embodiment, cap width 119 is up to 40 millimeters.

Figure 2:
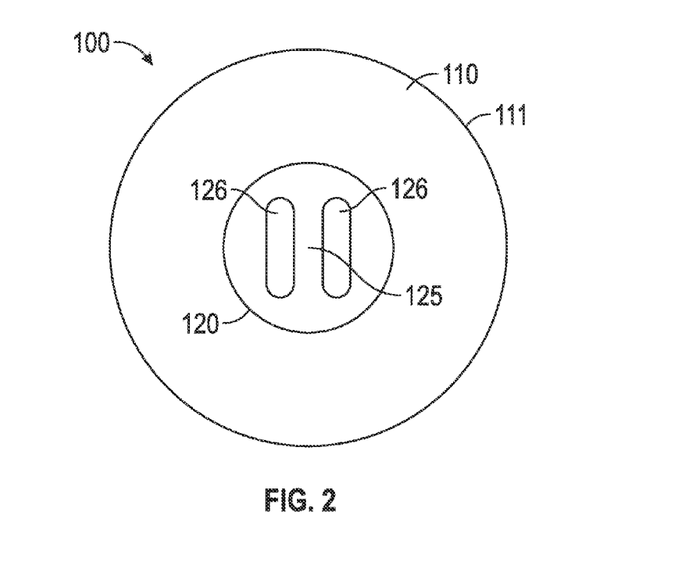
FIG. 2 is a bottom view of the cranial base implant device of FIG. 1.

Cap 110 includes a contact surface 114 and an upper surface 112. Contact surface 114 includes an outer perimeter 111. All or a portion of the outer perimeter 111 may be defined by cap width 119. In some embodiments, outer perimeter 111 is a circular shape as illustrated in FIG. 2. Contact surface 114 may have an annular shape, such as an annular surface. The outer diameter of the annular shape may match the outer perimeter 111. The inside diameter of the annular shape may match a diameter of stem 120.

Upper surface 112 includes an apex 113 spaced apart from the contact surface 114 at a cap height 118. The apex 113 may be a point or a surface. Upper surface 112 may extend from the apex 113 to the outer perimeter 111. In some embodiments, upper surface 112 extends from the apex 113 to the outer perimeter 111 in a curved manner. Upper surface 112 may have spherical, ellipsoidal or conical surface shape.

Cap 110 may be a spherical, ellipsoidal, spheroidal, or conical cap or frustum. A spherical, ellipsoidal, spheroidal, or conical frustum is the solid defined by cutting a sphere, ellipsoid, spheroid, or cone with a pair of parallel planes.

Stem 120 extends from cap 110. Stem 120 may extend from cap 110 at a stem length 128 and may extend in the direction opposite apex 113. Stem length 128 may be from 5 millimeters to 10 millimeters. Stem 120 may generally include a cylindrical shape and may include a stem width 129. The stem width 129 may be the largest width of the stem 120, such as the outer diameter of the cylindrical shape. Stem width 129 is generally smaller than cap width 119. Stem width 129 may be from 4 millimeters to 7 millimeters.

Stem 120 may include a body portion 122 and a neck portion 124. Body portion 122 may include a cylindrical shape with a diameter matching stem width 129. Neck portion 124 may extend between body portion 122 and contact surface 114. Neck portion 124 may include a diameter smaller than body portion 122 and may be smaller than stem width 129. The symmetry of upper surface 112, contact surface 114, body portion 122, and neck portion 124 may be about a single axis 105.

The diameter of neck portion 124 may match the inside diameter of contact surface 114. In the embodiment shown in FIG. 1, stem 120 extends from contact surface 114 in a direction perpendicular to contact surface 114.

In some embodiments, the cap 110 and the stem 120 may be symmetrical about the axis 105. The contact surface 114 and the stem 120 may also be aligned on axis 105. In other embodiments, the cap 110 and the stem 120 may be asymmetric. The various edges of the device 100 may be rounded. Stem 120 may be an integral piece to cap 110 or may be removable from cap 110.

FIG. 2 is a bottom view of the device 100 of FIG. 1. As illustrated in FIG. 2, device 100 may include a gripping feature 126. Gripping feature 126 may be located at the end of stem 120 distal to cap 110. In the embodiment illustrated in FIG. 2, gripping feature 126 includes adjacent recesses, such as slots extending into the end of stem 120 distal to cap 110 forming a ridge 125 there between. In other embodiments, ridge 125 may protrude from the end of stem 120 distal to cap 110. Gripping feature 126, and in particular ridge 125, may be configured for the interlocking of instruments such as Blakesly forceps and the like.

Figure 3:
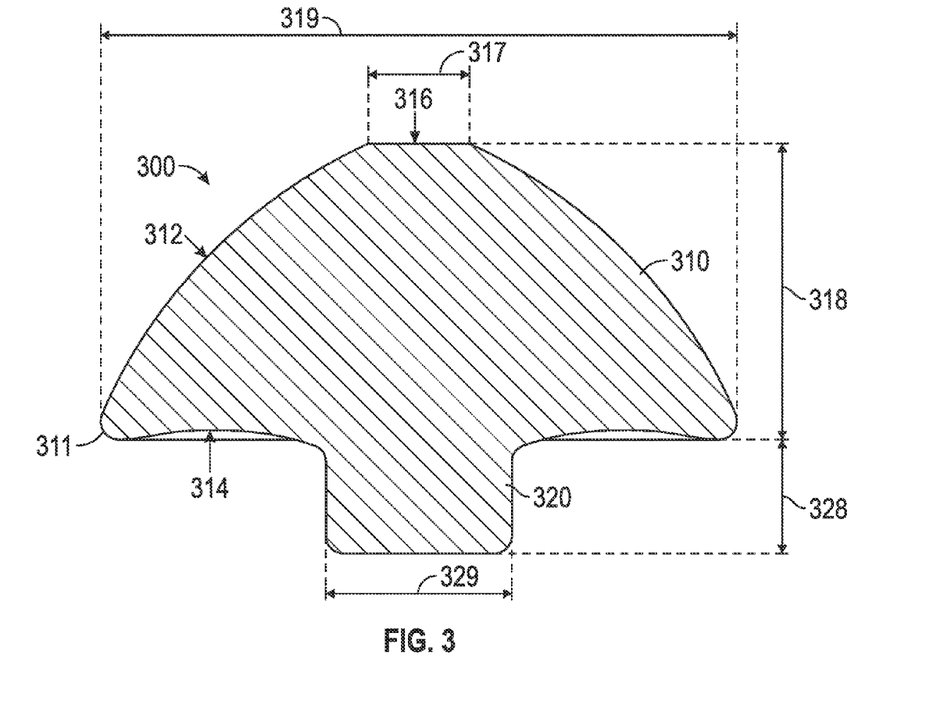
FIG. 3 is a cross-sectional view of an alternate embodiment of the cranial base implant device of FIG. 1.

FIG. 3 is a cross-sectional view of an alternate embodiment of the device 100 of FIG. 1. In the embodiment shown in FIG. 3, cap 310 of device 300 is rounded and includes a prolate spheroid frustum where the parallel planes cut through the major axis of the prolate spheroid on the same half of the prolate spheroid. In one embodiment, one parallel plane cuts through the prolate spheroid to define contact surface 314 and the other plane cuts through the prolate spheroid near or at the vertex of the prolate spheroid, forming tip surface 316. Tip surface 316 may be the apex of upper surface 312. The tip width 317 of tip surface 316 is smaller than the cap width 319.

In some embodiments, such as the embodiment illustrated in FIG. 3, contact surface 314 is an annular surface with a curved profile forming a concave surface that is revolved about stem 120. The various components and dimensions of device 300, such as cap width 319, cap height 318, stem width 329, and stem height 328 of device 300 may be the same or similar to the cap width 119, cap height 118, stem width 129, and stem height 128 as described in conjunction with device 100.

Figure 4:
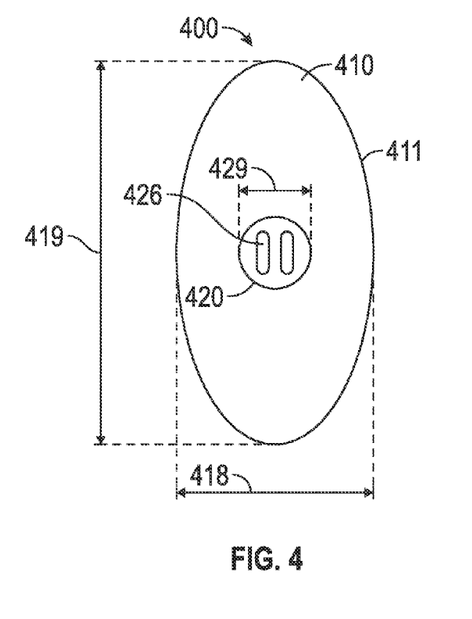
FIG. 4 is a bottom view of an alternate embodiment of the cranial base implant device of FIG. 1.

FIG. 4 is a bottom view of an alternate embodiment of the devices 100 of FIG. 1 and 300 of FIG. 3. In the embodiment illustrated, cap 410 includes an elliptical contact surface 414. Cap 410 may be an ellipsoidal cap or frustum, where the cutting surface(s) is parallel to the major axis of the ellipsoid, forming the elliptical outer perimeter 411 of contact surface 414. Cap 410 may include a major width 419 and a minor width 418. Major width 419 may be from 10 millimeters to 30 millimeters. Minor width 418 may be from 6 millimeters to 20 millimeters. Stem 420 may extend from the center of the contact surface 414. The various components and dimensions of device 400, such as cap height 418, stem width 429, stem height 428, stem 420, and gripping feature 426 of device 400 may be the same or similar to the cap width 119, cap height 118, stem width 129, and stem height 128 as described in conjunction with device 100.

Figure 5:
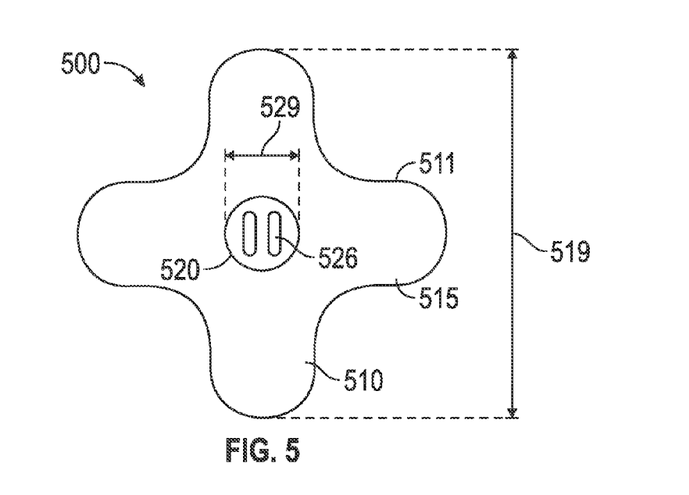
FIG. 5 is a bottom view of an alternate embodiment of the cranial base implant device of FIG. 1.

FIG. 5 is a bottom view of an alternate embodiment of the devices 100 of FIG. 1, 300 of FIG. 3, and 400 of FIG. 4. Device 500 includes multiple legs 515, where each leg 515 can be symmetrical to the other legs. The outer perimeter 511 may be defined by the shape of each leg 515.

Device 500 may include rotational symmetry. In the embodiment shown in FIG. 5, device 500 includes four rotationally symmetric legs 515. Each leg 515 may be a rounded solid with a flat surface on the bottom. Each leg 515 may converge with the other legs 515 at an apex forming a curved upper surface. In the embodiment illustrated, outer perimeter 511 includes the four legs 515 with each leg 515 including an arc at the end and the transition between adjacent legs 515 is also an arc.

The cap width 519 of device 500 may be from the edge of a first leg 515 to the edge of a second leg 515 opposite the first leg 515. The cap width 519 may be from 10 millimeters to 30 millimeters. The various components and dimensions of device 500, such as cap height 518, stem width 529, stem height 528, stem 520, and gripping feature 526 of device 500 may be the same or similar to the cap width 119, cap height 118, stem width 129, and stem height 128 as described in conjunction with device 100.

Any of the embodiments of the device, such as devices 100, 300, 400, and 500 as disclosed herein, herein after referred to as the device, and its various components, can be made out of a biocompatible material. The material may be a compressible and deformable material, such as an elastic material, that will regain its shape after being inserted into the sella turcica. The device may be a non-resorbable material such as open or closed cell foam, materials with suitable durometers such as silicone or elastomeric materials, or resorbable materials such as polylactic acid ("PLA"), polyglycolic acid ("PGA"), and hydrogel. The device may also be made from synthetic foams, polymers, plastics, or other medical grade materials. In some embodiments, the material of the device includes a hardness/durometer of Shore 20 A or softer, i.e. a hardness up to Shore 20 A. In other embodiments, the device includes a hardness from Shore 5 A to Shore 20 A. In yet another embodiment, the device includes a hardness between Shore 10 A and Shore 20 A.

The device may also be a combination or composite of a biomemetic component such as hydroxyapatite with any of the above mentioned materials. In some embodiments, the device may be formed out of a flexible, deformable organic material such as cartilage. The device may include a second material that acts as a marker for locating the device through imaging, such as computerized tomography, magnetic resonance, etc. The device may be opaque/colored or may be transparent/optically clear.

The device may be configured to allow for pressure relief, such as intracranial pressure relief. The device may also be configured to allow for injection of materials, such as a foam or gel, there through and into the sella turcica.

Figure 6:
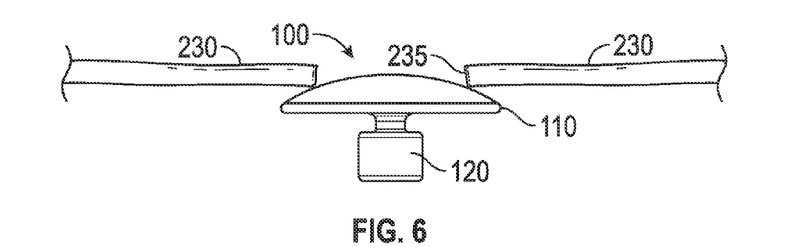
FIGS. 6-8 illustrate the cranial base implant device of FIG. 1 passing through a hole in the sphenoid bone.
Figure 7:
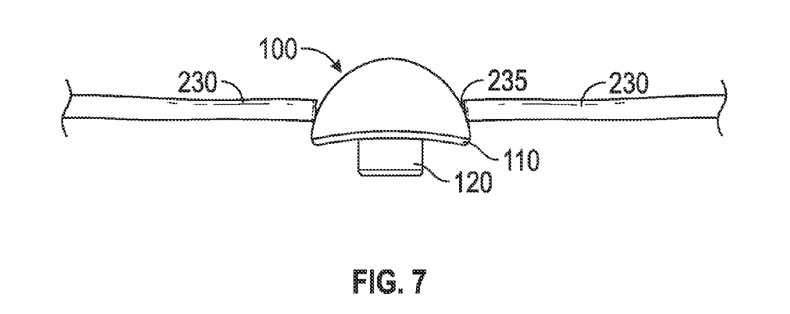
Figure 8:
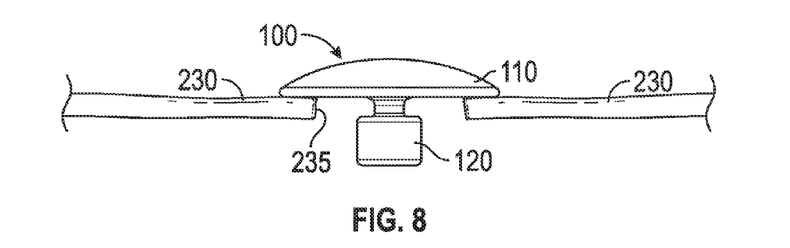

FIGS. 6-8 illustrate device 100 passing through hole 235 in the sphenoid bone 230. FIG. 6 illustrates device 100 as the tip of cap 110 initially contacts the sphenoid bone 230 at hole 235 prior to insertion of device 100 through hole 235. Prior to exerting force to pass device 100 through hole 235, device 100 maintains its original shape. FIG. 7 illustrates device 100 as it passes through hole 235. Hole 235 is smaller than the cap width 119. As device 100 passes through hole 235, cap 110 may compress, deform, and deflect inward and downward (toward stem 120). The cap width 119 may be temporarily smaller than the diameter of hole 235 as device 100 passes through hole 235.

FIG. 8 illustrates device 100 after device 100 passes through hole 235. After passing through hole 235, such as a defect in the sphenoid bone 230, device 100 may reshape, reform, and spring back into the same or a similar shape device 100 held prior to the insertion of device 100 through hole 235. The various embodiments disclosed herein, including devices 300, 400, and 500 may pass through hole 235 in the same or a similar manner as device 100. Any of the embodiments disclosed herein, may also be used for and passed through other skull based defects in different anatomic areas.

Figure 9:
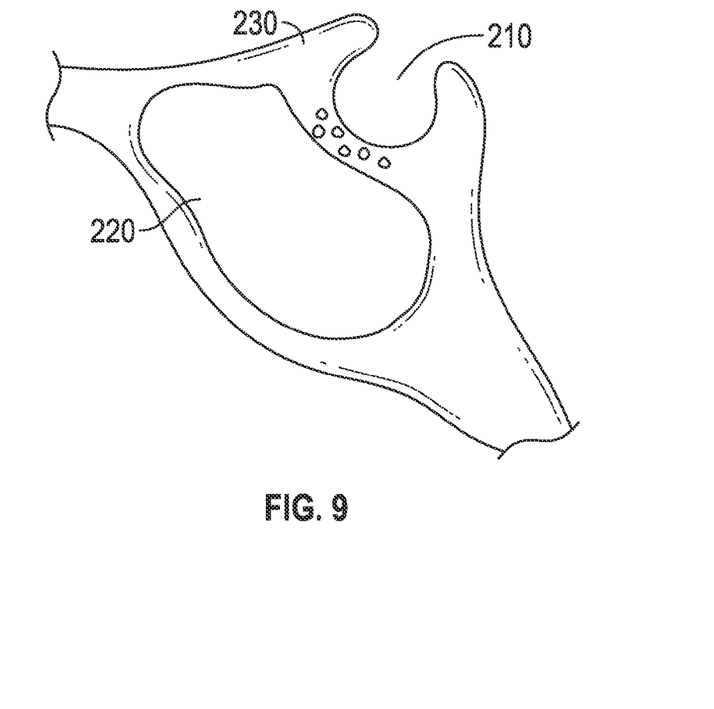
FIGS. 9-12 illustrate the insertion of the cranial base implant device into the sella turcica.
Figure 10:
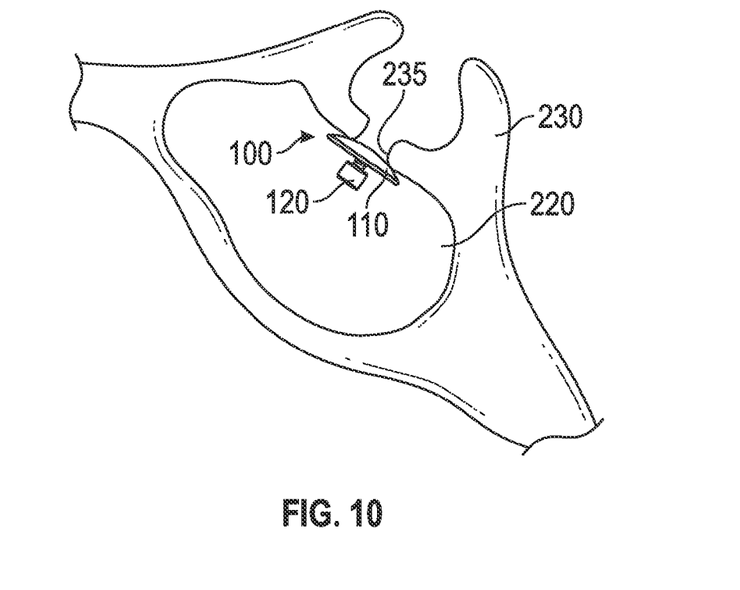
Figure 11:
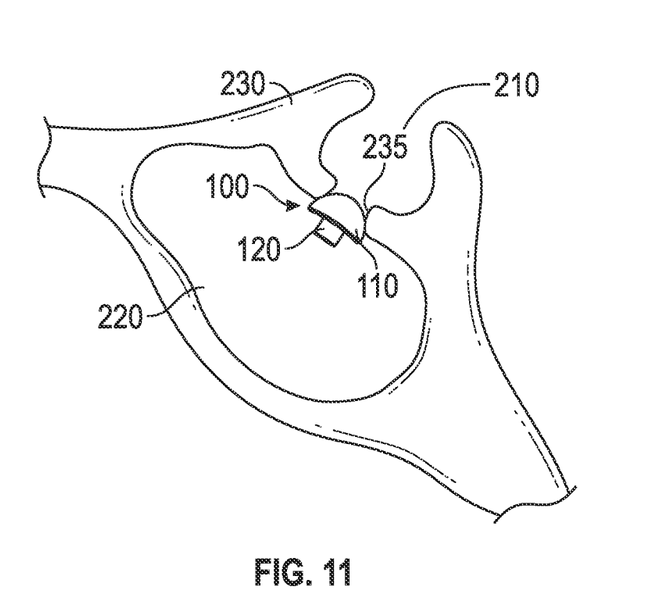
Figure 12:
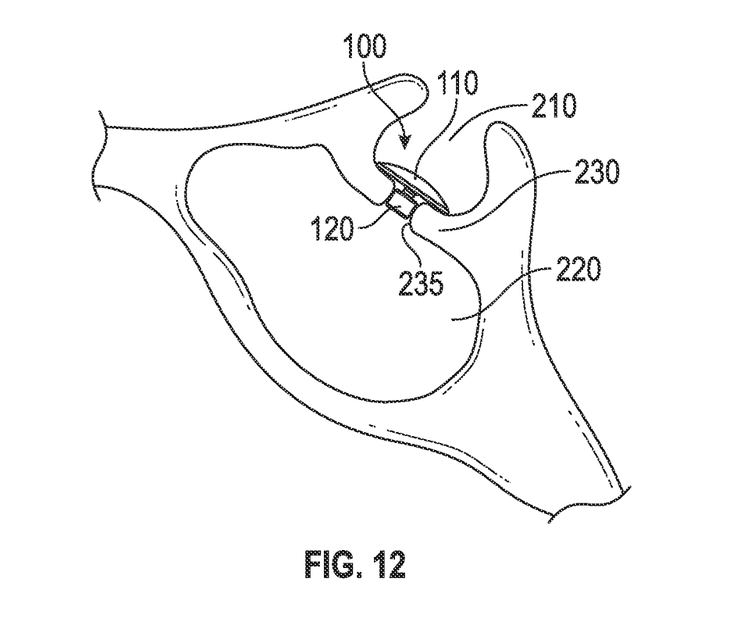

FIGS. 9-12 illustrate the insertion of device 100 into the sella turcica 210. As illustrated in FIG. 9, prior to surgery, the sella turcica 210 is separated from the sphenoid sinus 220 by the sphenoid bone 230. During surgeries such as endoscopic transphenoidal pituitary tumor removal a hole 235 is formed in the sphenoid bone 230 at the floor of the sella turcica 210. After the surgery is completed, the device 100 is located in an inlay position in the sella turcica 210 as illustrated in FIG. 12.

Figure 13:
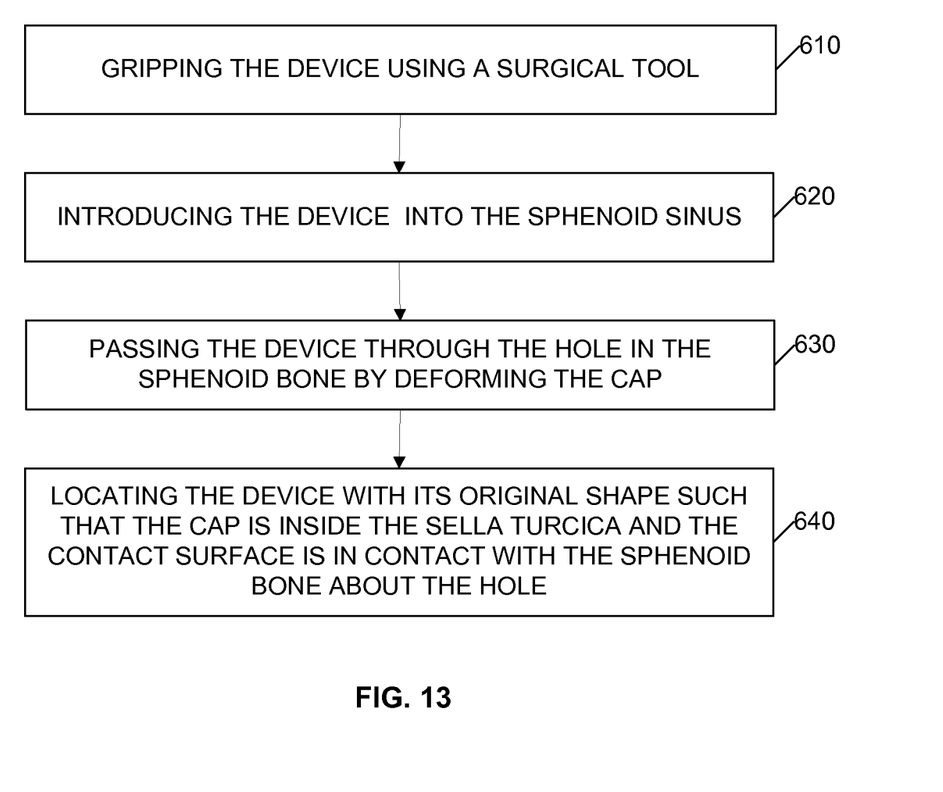
FIG. 13 is a flowchart of a method for locating the device 100 in an inlay position in the sella turcica 210.

FIG. 13 is a flowchart of a method for locating the device 100 in an inlay position in the sella turcica 210. The method includes gripping the device 100 using a surgical tool at step 610. The gripping feature 126 may be used to grip the device with the surgical tool. Step 610 is followed by introducing the device 100 into the sphenoid sinus 220 as illustrated in FIG. 10 at step 620. Step 620 is followed by passing the device 100 through the hole 235 in the sphenoid bone 230 by deforming the cap 110 as illustrated in FIG. 11 at step 630. As the leading point or tip of cap 110 is placed within hole 235, the outer perimeter 111 of cap 110 may deflect. The spherical, ellipsoidal, or conical shape of cap 110 may lead device 110 through hole 235 without the need for awkward maneuvers of placing a rigid bony or cartilaginous implant. Step 630 is followed by locating the device 100 with its original shape such that cap 110 is inside the sella turcica 210 and contact surface 112 is in contact with the sphenoid bone 230 about the hole 235 as illustrated in FIG. 12 at step 640. After passing through hole 235 the outer perimeter 111 deploys above and adjacent the edge of hole 235. This may result in the inner portion of contact surface 112 lying above hole 235. Device 100 may be held into place within the sella turcica 210 by the spinal fluid pressure and by gravity. The various embodiments of the device disclosed herein including devices 300, 400, and 500 may be located in an inlay position in the sella turcica 210 in the same or a similar method as device 100. The various embodiments of the device disclosed herein may be similarly located in other anatomical areas of the skull to plug or cover a skull based defect in those anatomical areas.

The compression, deformation, or deflection of the device may give the placement of the device within the sella turcica 210 the ease of placing an overlay graft. The elastic properties of the device providing for the reformation of the device into or near its original shape upon final placement may provide the structural support of an inlay graft. The device may widen gradually to its maximal width, allowing additional mass to be added at the cap, which may provide positional stability within the sella turcica 210.

The stem of the device may be used for placement and retrieval of the device and may also be used for providing an element of overlay support by itself or in conjunction with a small amount of adjunctive material such as foam or surgical glue. The gripping feature may facilitate the interlocking of surgical instruments, such as Blakesly forceps during placement and retrieval of the device. Further, the device may contain or elute medicinal substances/agents, such as drugs, biologics, for the treatment of underlying disease or for the promotion of healing or other purposes.

The device may prevent or reduce the risk of cerebrospinal fluid leaks during or after transphenoidal surgeries such as endoscopic transphenoidal pituitary tumor removal. The use of the device may reduce the costs and duration of transphenoidal surgeries by providing a readily available implant that does not require processing prior to or during the surgery as is the case with bone, cartilage, and tissue implants.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art.

We claim:

1. A device for covering a hole in a sphenoid bone between a sella turcica and a sphenoid sinus, the device comprising:
   a cap formed of a deformable material configured to deform and pass through the hole in the sphenoid bone during insertion into the sella turcica and configured to reform after insertion into the sella turcica, the cap including
      a contact surface forming a base of the cap, the contact surface including an outer perimeter configured to be larger than the hole in the sphenoid bone, the contact surface being configured to contact the sphenoid bone in an inlay position after insertion into the sella turcica, and
      an upper surface including an apex offset from the contact surface at a cap height, the upper surface extending from the apex to the outer perimeter; and
   a stem extending from the contact surface in a direction opposite the apex and configured to be gripped by a surgical instrument during insertion of the cap into the sella turcica.

2. The device of claim 1, wherein the deformable material is an elastic material.

3. The device of claim 1, wherein the deformable material includes a hardness up to Shore 20 A.

4. The device of claim 1, wherein the upper surface extends from the apex to the outer perimeter in a curved manner.

5. The device of claim 1, wherein the upper surface includes a spherical cap shape.

6. The device of claim 5, wherein the contact surface is an annular surface and the stem includes a cylindrical surface extending from an inner diameter of the contact surface.

7. The device of claim 6, wherein the contact surface and the stem are aligned on a single axis.

8. The device of claim 1, wherein the stem includes a body portion with a first cylindrical shape including a first diameter and a neck portion extending between the cap and the body portion with a second cylindrical shape, the second cylindrical shape including a second diameter smaller than the first diameter.

9. The device of claim 1, further comprising a gripping feature located at an end of the stem distal to the cap.

10. The device of claim 9, wherein the gripping feature includes a ridge.

11. The device of claim 10, wherein the ridge is formed by adjacent recesses in the end of the stem distal to the cap.

12. The device of claim 1, wherein a radius of the upper surface is larger than the cap height.

13. The device of claim 1, wherein the cap is a frustum and includes a tip surface at the apex, the tip surface being parallel to the contact surface and spaced apart from the contact surface at the cap height.

14. The device of claim 1, wherein the cap is an ellipsoid and the contact surface is an elliptical surface where the cap width is a major axis from 10 millimeters to 30 millimeters and the contact surface also includes a minor axis from 6 millimeters to 20 millimeters.

15. The device of claim 1, wherein the cap include multiple legs converging together forming the upper surface, each leg including a flat surface that forms a portion of the contact surface.

16. The device of claim 1, wherein the stem is removable.

17. The device of claim 1, further comprising a second material that acts as a marker for location of the device through imaging.

18. A device for closing a hole in a sphenoid bone that acts as a barrier between a sella turcica and a sphenoid sinus, the device comprising:
   a cap with a spherical cap shape, the cap including
      an upper surface with a spherical shape, and
      a contact surface forming a base of the spherical cap shape, the contact surface being an annular surface; and
   a stem extending from the contact surface in a direction opposite the upper surface;
   wherein the cap is configured to compress and deflect inward and downward toward the stem when passing through the hole in the sphenoid bone and to reform and cover the hole in an inlay position after passing through the hole; and
   wherein the stem is configured to be gripped by a surgical instrument during insertion and removal of the device.

19. The device of claim 18, wherein the stem includes a body portion with a first cylindrical shape including a first diameter, and a neck portion extending between the cap and the body portion with a second cylindrical shape, the second cylindrical shape including a second diameter smaller than the first diameter.

20. The device of claim 18, wherein the upper surface and the contact surface intersect at an outer perimeter.

21. The device of claim 18, wherein the cap includes a cap width from 6 millimeters to 40 millimeters, the cap width being a diameter of the cap at an intersection of the upper surface and the contact surface.

22. The device of claim 18, wherein the stem includes a stem width from 4 millimeters to 7 millimeters.

23. The device of claim 18, wherein the stem extends from the cap from 5 millimeters to 10 millimeters.

24. The device of claim 18, further comprising a gripping feature located at an end of the stem distal to the cap, the gripping feature including slots forming a ridge there between.

25. The device of claim 18, wherein the cap is formed from a material with a hardness up to Shore 20 A.

26. The device of claim 18, wherein the device is configured to elute medicinal substances.

27. The device of claim 18, wherein the device is configured to allow for intracranial pressure relief.

28. The device of claim 18, wherein the device is configured to allow for injection of materials into the sella turcica.

29. A method for locating a device in an inlay position in the sella turcica, the device including a cap formed of deformable material and a stem extending from the cap, the method comprising:
   gripping the device using a surgical tool;
   introducing the device into the sphenoid sinus;
   passing the device through a hole in the sphenoid bone by deforming the cap; and
   locating the device with its original shape such that the cap is inside the sella turcica and a contact surface of the cap is in contact with the sphenoid bone about the hole.

30. The method of claim 29, wherein gripping the device using a surgical tool includes gripping a ridge of a gripping feature located at an end of the stem distal to the cap.

* * * * *